United States Patent [19]

Steen et al.

[11] 4,026,825

[45] May 31, 1977

[54] FOAMING AND CONDITIONING DETERGENT COMPOSITION

[75] Inventors: Howard Robertson Steen; Henry Trainor, both of Newcastle upon Tyne, England

[73] Assignee: The Procter & Gamble Company, Cincinnati, Ohio

[22] Filed: June 11, 1975

[21] Appl. No.: 585,936

[30] Foreign Application Priority Data

June 14, 1974 United Kingdom ............ 26475/74

[52] U.S. Cl. ............................... 252/547; 252/548; 252/550; 252/551; 252/555; 252/557; 252/558; 252/DIG. 14

[51] Int. Cl.² ..................... C11D 1/00; C11D 3/32; C11D 17/02

[58] Field of Search .............. 252/551, 90, 89, 308, 252/550, 554, 555, 558, 545–547; 424/358

[56] References Cited

UNITED STATES PATENTS

| | | | |
|---|---|---|---|
| 2,543,061 | 2/1951 | Rider et al. | 252/313 X |
| 3,011,950 | 12/1961 | Mehaffey | 252/90 X |
| 3,419,658 | 12/1968 | Sanders | 424/45 |
| 3,528,925 | 9/1970 | Chapuis | 252/90 X |
| 3,533,955 | 10/1970 | Pader et al. | 252/153 |
| 3,548,056 | 12/1970 | Eigen et al. | 424/171 |
| 3,719,752 | 3/1973 | Taylor | 424/47 |
| 3,728,265 | 4/1973 | Cella et al. | 252/90 |
| 3,798,179 | 3/1974 | Hellyer | 252/535 |

FOREIGN PATENTS OR APPLICATIONS

| | | |
|---|---|---|
| 1,948,800 | 1/1971 | Germany |
| 684,784 | 1/1969 | South Africa |

OTHER PUBLICATIONS

Branday, "Cosmetic Surfactants in this Detergents Age," Detergent Age, 1969.

*Primary Examiner*—P.E. Willis, Jr.
*Attorney, Agent, or Firm*—Douglas C. Mohl; Ronald L. Hemingway; Richard C. Witte

[57] ABSTRACT

This invention relates to a foaming and conditioning composition, especially a liquid detergent conditioning composition having a low viscosity and able to provide in the bath tub a desirable quantity of suds and water-insoluble oil material having skin-softening or emollient properties.

14 Claims, No Drawings

FOAMING AND CONDITIONING DETERGENT COMPOSITION

DISCUSSION OF THE INVENTION

The preparation of compositions adapted to use in bathing is well known in the art. Such compositions have typically included liquid bath oil compositions which are added to bath water to provide a layer of oily emollient on the surface of the bath water. Such compositions provide an anointing or skin softening quality to alleviate dry skin conditions and to prevent excessive moisture loss from the skin after bathing. Other bath compositions have included bubble bath formulations comprised of a water-soluble detergent active base to provide a copious quantity of bubbles or foam.

Various attempts have been made in the art to provide bath compositions designed to combine the desirable foaming properties of a bubble bath composition with the emollient properties of a bath oil. Inasmuch as the desirable sudsing, cleaning, wetting, solubilization, emulsification and dispersion properties characteristic of surfactants are mutually antagonistic with the emolliency and deposition properties of oleaginous materials, such attempts have not been entirely satisfactory. Thus, attempts to provide detergent compositions embodying these desirable properties have been characterized by the attainment of either copious foam formation with little emollient effect or desirable emollient qualities with low levels of foam formation. The mutually antagonistic properties of foam formation and emolliency have been referred to by T. Kaufman in *American Perfumer and Cosmetics*, Vol. 80, pages 29 to 31 (Feb. 1965). The formulation of a foaming bath oil representing a "compromise" to the attainment of copious foam formation and emolliency is described.

One approach to the provision of foaming bath oil compositions has involved physical separation of the foaming and emollient components, as by microencapsulation, so as to provide separate introduction of these components into the bath water and is described in South African patent application 68/4784 to Randerbrock et al. U.S. Pat. No. 3,533,955 (Oct. 13, 1970) to Pader et al described a two-phase liquid detergent composition having a detergent, emollient, water and emulsion destabilizer. Encapsulation necessarily adds to the cost of foaming bath oils while demulsification properties may depend on the amount of demulsifier employed.

Compositions which are similar to those of the present invention are known and described in the copending British patent application 2903/74 Jan. 22, 1974) in the name of Melvin A. Barbera entitled "Foaming and conditioning detergent composition".

The present invention relates to a substantially anhydrous foaming and conditioning composition providing suds and a layer of emollient oil upon addition to water comprising a mutually insoluble mixture of a water-soluble foaming organic detergent and a water-insoluble oily material having skin-softening or emollient properties, the mutual insolubility being such that neither the detergent nor the oily material is soluble in the other in an amount greater than 0.1% by weight of the said other, the viscosity of the composition being less than 500 centipoises, and the organic detergent being in the form of finely divided particles containing at least 50% by weight of organic surfactant, and having a moisture content of less than 5% by weight, at least 90%, preferably at least 95% of the particles being of a size to pass a 100 mesh screen and at least 50% of the particles being of a size to pass a 200 mesh screen, the particles having a bulk density of at least 0.4 g/cc.

The compositions of this invention have been found to give improved storage stability compare to the compositions of British Application 2903/74 and their lower inherent viscosity permits more flexibility in formulation. The detergent particles are generally faster dissolving than the spray dried particles of that application and may disperse almost immediately when the composition is added to water.

The detergent compositions of the invention by virtue of the small size of the detergent particles and the higher bulk density of said particles have a low viscosity compared to similar compositions prepared from, e.g., spray dried detergent granules which have a large particle size and/or lower bulk density. This results from the higher bulk density which permits incorporation of a greater amount of detergent with less volume. The lower viscosity also results from the very small particle size of the detergent particles.

In order that the compositions of the invention will exhibit the desirable properties described hereinbefore it is essential that the particle size of the detergent particles be such that at least 90% of said particles will pass through a 100 mesh screen and that at least 50% of said particles will pass a 200 mesh screen. Preferably at least 75% of said particles will pass through a 200 mesh screen and more preferably at least 90% of said particles will pass through a 200 mesh screen.

As will be discussed hereinafter the detergent particles of this invention contain at least 50% organic surfactant. In order to obtain the very small particle sizes required by the compositions of this invention in an economical manner it is desirable to resort to freeze grinding of drum-dried detergent flakes. In freeze grinding the detergent flakes are cooled, e.g., by the application of liquid nitrogen, before being milled or ground to obtain the correct particle size distribution. Since milling or grinding generates heat and since the surfactants of this invention are plastic materials it is extremely difficult to reduce larger particles to the proper particle size without first chilling the particles. This chilling can be done by any means but a convenient way is to use liquid nitrogen.

Other method of size reduction can be used if they result in the proper particle size and the proper bulk density.

The bulk density is important since the volume of the particles is related directly to the bulk density. The smaller the volume of the detergent particles the lower will be the viscosity.

The detergent particles of this invention contain less than 5% moisture by weight, preferably less than 2% and most preferably less than 1%. Low moisture is important in order to prevent dissolution of the surfactant in the emollient.

The detergent material of this invention must be selected to have the correct solubility characteristics.

The solubility characteristics can be readily determined by resort to known solubility and analytical techniques, the particular method employed depending upon the particular surfactants or emollients considered, their physical characteristics and the like. Solid or particulate foaming surfactants will generally be added to a liquid emollient oil at 30° C and the amount dissolved expressed as a percentage by weight of the emollient oil. The mutual solubility characteristics of liquid surfactants and emollient oils will normally be determined by measuring the solubility of each material in the other so as to determine the suitability or compatibility of the materials for combination and provision of the desirable and respective foaming and emolliency effects.

The detergent particles of this invention contain at least 50% by weight organic detergent (surfactant), preferably the particles contain at least 75% organic surfactant and most preferably the detergent particles contain at least 90% organic surfactant.

Detergents suitable herein are water-soluble foaming organic detergents selected from anionic, nonionic, cationic, zwitterionic and amphoteric classes. Suitable detergent materials are those which provide copious suds-formation and cleansing properties. It will be appreciated that a given surfactant material may provide desirable suds formation and cleansing properties, but may be soluble or insoluble in the emollient oil, as defined hereinbefore, depending on the particular nature of the emollient considered. Thus, a foaming surfactant may be insoluble in mineral oil and permit the attainment simultaneously of the desired objectives of copious suds formation and skin deposition in bath use, but may be soluble, for example in olive oil and, thus, be unsuited for a composition of the invention where it is desirable that olive oil be employed as the emollient component. Compatible combinations of foaming surfactant and emollient, i.e. those which will permit the attainment of both suds formation and skin-oiling effects in bathtub use, can, however, be determined by the mutual solubility or insolubility characteristics described hereinbefore. Suitable combinations can, thus, be easily determined.

Examples of surfactant materials from which the foaming and oil-insoluble detergents of the invention can be selected include the water-soluble anionic, nonionic, cationic, zwitterionic and amphoteric detergents described as follows:

a. Anionic detergents include the synthetic non-soap detergents which can be broadly described as the water-soluble salts, particularly the alkali metal salts, of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the synthetic detergents which form a part of the compositions of the present invention are the alkali metal, e.g. sodium or potassium, alkyl sulfates, especially those obtained by sulfating the higher alcohols ($C_8$–$C_{18}$ carbon atoms) produced by reducing the glycerides of tallow or coconut oil; the alkali metal olefin sulfonates of from 8 to 24 carbon atoms described, for example, in U.S. Pat. No. 3,332,880, issued July 25, 1967 to Philip E. Pflaumer and Adriaan Kessler; and the alkali metal alkyl glyceryl ether sulfonates, especially those ethers of the higher alcohols derived from tallow and coconut oil; other anionic detergents include the alkali metal alkylbenzene sulfonates, in which the alkyl group contains from about 9 to about 15 carbon atoms, including those of the types described in U.S. Pat. Nos. 2,220,099 and 2,477,383 (the alkyl radical can be a straight or branched aliphatic chain); sodium coconut oil fatty acid monoglyceride sulfates and sulfonates; sodium or potassium salts or sulfuric acid esters of the reaction product of one mole of a higher fatty alcohol (e.g., tallow or coconut oil alcohols) and about 1 to 6 moles of ethylene oxide; sodium or potassium salts of alkyl phenol ethylene oxide ether sulfate with about 1 to about 10 units of ethylene oxide per molecule and in which the alkyl radicals contain from 8 to about 12 carbon atoms; the reaction product of fatty acids esterified with isethionic acid and neutralized with sodium hydroxide where, for example, the fatty acid is oleic or derived from coconut oil; sodium or potassium salts of fatty acid amide of a methyl tauride in which the fatty acids, for example, are derived from coconut oil; sodium or potassium $\beta$-acetoxy- or $\beta$-acetamidoalkanesulfonates where the alkane has from 8 to 22 carbon atoms; and others known in the art, a number specifically set forth in U.S. Pat. Nos. 2,486,921, 2,486,922 and 2,396,278.

b. Nonionic synthetic detergents: One class can be broadly defined as compounds produced by the condensation of alkylene oxide groups (hydrophilic in nature) with an organic hydrophobic compound, which can be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements. Another class has semi-polar characteristics. Classes of nonionic synthetic detergents are as follows:

1. A class of nonionic synthetic detergents under the trade name of "pluronic." These compounds are formed by condensing ethylene oxide with a hydrophobic base formed by the condensation of propylene oxide with propylene glycol. The hydrophobic portion of the molecule which, of course, exhibits water insolubility, has a molecular weight of from about 1500 to 1800. The addition of polyoxyethylene radicals to this hydrophobic portion tends to increase the water solubility of the molecule as a whole and the liquid character of the product is retained up to the point where the polyoxyethylene content is about 50% of the total weight of the condensation product.

2. The polyethylene oxide condensates of alkyl phenols, e.g., the condensation products of alkyl phenols having an alkyl group containing from about 6 to 12 carbon atoms in either a straight chain or branched chain configuration with ethylene oxide, the said ethylene oxide being present in amounts equal to 5 to 25 moles of ethylene oxide per mole of alkyl phenol. The alkyl substituent in such compounds may be derived from polymerized propylene, diisobutylene, octene, or nonene, for example.

3. Those nonionic synthetic detergents derived from the condensation of ethylene oxide with the product resulting from the reaction of propylene oxide and ethylene diamine. For example, compounds containing from about 40 to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide; said base having a molecular weight of the order of 2,500 to 3,000 are satisfactory.

4. The condensation product of aliphatic alcohols having from 8 to 22 carbon atoms, in either straight chain or branched chain configuration, with ethylene oxide, e.g., a coconut alcohol ethylene oxide condensate having from 5 to 30 moles of ethylene oxide per mole of coconut alcohol, the coconut alcohol fraction having from 10 to 14 carbon atoms.

5. The ammonia, monoethanol and diethanol amides of fatty acids having an acyl moiety of from about 8 to about 18 carbon atoms. These acyl moieties are normally derived from naturally occurring glycerides, e.g., coconut oil, palm oil, soybean oil and tallow, but can be derived synthetically, e.g., by the oxidation of petroleum, or by hydrogenation of carbon monoxide by the Fischer-Tropsch process.

6. Long chain tertiary amine oxides corresponding to the following general formula

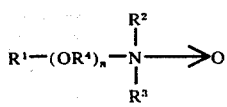

wherein $R^1$ is an alkyl radical of from about 8 to about 24 carbon atoms, $R^2$ and $R^3$ are each methyl, ethyl or hydroxyethyl radicals, $R^4$ is ethylene, and $n$ equals from 0 to about 10. The arrow in the formula is a conventional representation of a semi-polar bond. Specific examples of amine oxide detergents include: dimethyldodecylamine oxide; cetyldimethylamine oxide; bis-(2-hydroxyethyl) dodecylamine oxide; and bis-(2-hydroxyethyl)-3-dodecoxy-1-hydroxypropyl amine oxide.

7. Long chain tertiary phosphine oxides corresponding to the following general formula $RR'R''P \rightarrow O$ wherein R is an alkyl, alkenyl or monohydroxyalkyl radical ranging from 10 to 24 carbon atoms in chain length and R' and R'' are each alkyl or monohydroxyalkyl groups containing from 1 to 3 carbon atoms. The arrow in the formula is a conventional representation of a semi-polar bond. Examples of suitable phosphine oxides are found in U.S. Pat. No. 3,304,262 of Feb. 14, 1967 and include: dimethyldodecylphosphine oxide; diethyldodecylphosphine oxide; dimethyl-(2-hydroxydodecyl) phosphine oxide.

8. Long chain sulfoxides having the formula

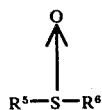

wherein $R^5$ is an alkyl radical containing from about 10 to about 28 carbon atoms, from 0 to about 5 ether linkages and from 0 to about 2 hydroxyl substituents, at least one moiety of $R^5$ being an alkyl radical containing 0 ether linkages and containing from about 10 to about 18 carbon atoms, and wherein $R^6$ is an alkyl radical containing from 1 to 3 carbon atoms and from one to two hydroxyl groups. Specific examples of these sulfoxides are: dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

c. Amphoteric synthetic detergents can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Examples of compounds falling within this definition are sodium-3-dodecylaminopropionate and sodium-3-dodecylaminopropane sulfonate.

d. Zwitterionic synthetic detergents can be broadly described as derivatives of aliphatic quaternary ammonium, phosphonium, and sulfonium compounds, in which the aliphatic radical may be straight chain or branched, and wherein one of the aliphatic substituents contains from about 8 to 18 carbon atoms and one contains an anionic water solubilizing group, e.g., carboxy, sulfo, sulfato, phosphato, or phosphono. Examples of compounds falling within this definition are 3-(N,N-dimethyl-N-hexadecylammonio) propane-1-sulfonate and 3-(N,N-dimethyl-N-hexadecylammonio)-2-hydroxy propane-1-sulfonate.

e. Cationic detergents include those having the formula $R - N(R^2)_3^{(+)}X^{(-)}$ wherein R is an alkyl chain containing from about 8 to about 20 carbon atoms, each $R^2$ is selected from the group consisting of alkyl and alkanol groups containing from 1 to 4 carbon atoms and benzyl groups there being normally no more than one benzyl group and two $R^2$ groups can be joined by either a carbon-carbon ether, or imino linkage to form a ring structure, and X represents a halogen atom, sulfate group, nitrate group or other pseudohalogen group. Specific examples are coconut alkyl trimethyl amine chloride, dodecyl dimethyl benzyl bromide, and dodecyl methyl morpholino chloride.

Especially preferred herein are water-soluble synthetic detergents which exhibit desirable scum-dispersing properties. Inasmuch as bar soaps are usually employed for cleansing the skin while bathing, the presence of a curd-dispersing surfactant in the compositions of the invention is preferred. The presence of hardness in the bath water frequently causes the formation of soap curd which, in combination with an emollient bath oil and body soils or lipids, can result in the formation of unsightly curd-like material floating on the surface of the water and collecting as hard-to-remove ring around the bathtub. The use of a detergent component capable of dispersing any such soap curds constitutes a preferred aspect of the present invention. Preferred curd-dispersing surfactants herein include the alkali metal, e.g., sodium, alkyl glyceryl ether sulfonates having from 10 to 18 carbon atoms in the alkyl group, especially those ethers of the higher alcohols derived from tallow and coconut oil; and the long-chain tertiary amine oxide detergents exemplified hereinbefore. These curd-dispersing detergents provide copious foam formation in bathtub use and are virtually insoluble in a preferred emollient, mineral oil. Other curd-dispersing detergents include the condensation products of aliphatic alcohols having from 8 to 22 carbon atoms with ethylene oxide; the alkali metal β-acetamido-alkanesulfonates and the fatty acid esters of alkali metal isethionates and the alkali metal salts of sulfuric acid esters of the reaction product of one mole of a higher fatty alcohol (e.g., tallow or coconut oil alcohols) with about 1 to 6 moles of ethylene oxide.

The water-soluble synthetic detergent of the compositions of the invention is employed in an amount sufficient to provide desired suds formation under normal usage conditions. In some instances copious suds formation will be desired while in others a bathing composition providing less sudsing effects may be preferred by the user. Depending upon the foaming capacity and amount of the particular detergent employed, desirable variations can be obtained. Normally the detergent component will comprise from about 10 to 60% by weight of the composition. Preferably, the detergent comprises from 20 to 50% by weight of the composition. While some users will tend to use more or less of the compositions of the invention than others, the use of a sufficient amount to provide about 0.4 g. of a copious foaming detergent per gallon of bath tub water will normally be sufficient to provide desired suds formation.

Mixtures of detergent compounds can be employed where desired. A preferred detergent combination comprises an alkali metal alkyl glyceryl ether sulfonate having from 10 to 18 carbon atoms in the alkyl group and an amine oxide detergent having one alkyl of from 8 to 24 carbon atoms and two short-chain alkyl groups. Such a combination is virtually insoluble in mineral oil. Dispersed in mineral oil, it provides desirable suds formation and permits the formation of a stable viscous composition exibiting uniform viscosity upon storage.

A further preferred detergent composition comprises a water-soluble, scum dispersing synthetic detergent, for instance, an alkali metal alkyl glyceryl ether sulphonate having from 10 to 18 carbon atoms in the alkyl group, together with a fatty acid mono- or di-alkanolamide, or a mixture of the two. The fatty acid alkanolamides act to increase the initial level and the stability of suds formed when a sample of the composition is dispersed in water. Preferably, the composition comprises a mixture of lauric monoethanolamide and lauric diethanolamide, this combination giving good initial suds height and suds stability in both soft and hard water. The amides are generally used in a weight ratio lying between 10 to 1 to 1 to 1, but a ratio of 2 to 1 has been found to be particularly effective. The alkali metal alkyl glyceryl ether sulphonate by itself is also a preferred detergent.

It will be recognized that some of the above detergents will be liquids in the pure form. In such instances, a sufficient amount of an inorganic material will be added to the detergent to make the mixture a solid at room temperature.

As stated hereinbefore, the water soluble detergent component is admixed or distributed through the emollient continuum in the form of very small particles. These particles can contain a water-soluble organic or inorganic builder salt. Builder salts serve as a convenient carrier or vehicle for the water soluble detergent component and serve as a desirable moisture sink. In some cases they help stabilize suds or foam against collapse when soap is dissolved in the bath water and minimise the formation of sticky lime soap bar curds.

Suitable water-soluble inorganic alkaline builder salts that can be employed alone or in admixture are the alkali metal carbonates, borates, phosphates, polyphosphates, bicarbonates and silicates. The ammonium or substituted-ammonium salts can also be employed. Specific examples of suitable builder salts include sodium tripolyphosphate, sodium carbonate, sodium tetraborate, sodium pyrophosphate, sodium acid pyrophosphate, sodium bicarbonate, potassium tripolyphosphate, potassium pyrophosphate, sodium hexametaphosphate, sodium sesquicarbonate, sodium mono- and di-orthophosphate and potassium bicarbonate.

Examples of water-soluble organic alkaline sequestrant builder salts used alone or in admixture are alkali metal, ammonium or substituted-ammonium, aminopolycarboxylates, e.g., sodium and potassium ethylenediaminetetraacetate, sodium and potassium N-(2-hydroxyethyl)-ethylenediaminetriacetates, sodium and potassium nitrilotriacetates and sodium, potassium and triethanolammonium, N-(2-hydroxyethyl)-nitrilodiacetate. Other organic alkaline sequestrant builder salts which can be used are: hydroxyethylethylenediaminetriacetates; 2-hydroxyethyliminodiacetates, diethylenetriaminepentaacetates; 1,2-diaminocyclohexanetetraacetates and the alkali metal citrates. Mixed salts of these polycarboxylates are also suitable. The alkali metal salts of phytic acid e.g. sodium phytate are also suitable as organic alkaline sequestrant builder salts (see U.S. Pat. No. 2,739,942).

Inasmuch as the compositions of the invention will be in contact with the skin of the user the detergent component will be formulated to provide a pH in use within the range of from about 4 to about 10, depending upon the particular detergent or material employed. Preferably, a pH in the range of 5 to 8 is provided.

The emollient component of the compositions of the invention comprises a water-insoluble and/or water-immiscible oily material having a skin softening or conditioning properties. Suitable emollient materials which can be employed herein are those which combine with a foaming surfactant in a relation of mutual insolubility and include emollient materials known in the bath oil arts. These include light-to-heavy mineral or hydrocarbon oils, vegetable oils, such as olive oil, arachid oil, sesame oil, castor oil, peanut oil, almond oil, sunflower oil, safflower oil cottonseed oil, coconut oil, synthetic esters such as isopropyl myristate, isopropyl palmitate, isopropyl stearate, decaglycerol, decalinoleate and the lanolin and chloresterol derivatives such as the lanolin alcohols and esters and silicone oils. Preferred emollients include mineral oil having a viscosity of from about 20 cp to 200 cp and isopropyl myristate which are readily available and in which preferred foaming surfactants such as alkyl glyceryl ether sulfonates, amine oxides and olefin sulphonates are virtually insoluble. Especially preferred are mixtures of mineral oil and isopropyl myristate, e.g. 20% mineral oil/80% isopropyl myristate.

The emollient component will normally be admixed with the foaming surfactant described hereinbefore in an amount of from 40 to about 90%. Use of less than about 40% tends to give a product which is not sufficiently fluid, while amounts greater than about 90% provide little additional benefit and limit the amount of the detergent component that may be accommodated. The relative amounts of emollient and detergent component can, however, be varied according to the relative degrees of emollient deposition on the skin, sudsing and curd-dispersion properties desired and the inherent foaming and skin-depositing or conditioning properties of the particular materials employed. The emollient will preferably be employed in an amount of from 50 to about 80% of the compositions of the invention.

The extent to which the compositions of the invention will provide foaming and skin depositing or conditioning properties will depend upon the degree to which the respective foaming and emollient compounds exhibit their respective properties in the absence of incompatible or antagonistic material and upon the degree of incompatibility or solubility when employed in combination. Combinations of foaming surfactant and emollient material will permit maximum realization of the inherent properties of the respective components where the materials are mutually insoluble as defined hereinbefore. Best results are achieved where the solubility is less than 0.01%. Combinations of surfactants which exhibit low orders of mutual solubility include the following at a 50/50 by weight proportion: sodium coconut-alkyl glyceryl ether sulfonate and mineral oil; lauric diethanolamide and mineral oil; dimethyl coconut-alkyl amine oxide and mineral oil; oleic acid ester of sodium isethionate and olive oil; sodium α-olefin sulfonate and mineral oil; potassium coconut-alkyl sulfate and mineral oil; and potassium coconut-alkyl sulfate and isopropyl myristate.

Preferred combinations of the invention are those which include a surfactant which exhibits a high intrinsic capacity for foam formation in aqueous solution and which is insoluble in the emollient oil. Such combinations are preferred from the standpoints of their copious foaming properties and their emolliency effects and include compositions comprising: from 20% to 60% of a water-soluble foaming organic detergent selected from the group consisting of alkali metal alkyl glyceryl ether sulfonates having from 10 to 18 carbon atoms in the alkyl group; long-chain tertiary amine oxides having the formula

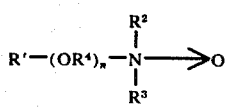

wherein R' is alkyl of from 8 to 24 carbon atoms, $R^2$ and $R^3$ are each methyl, ethyl or hydroxyethyl, $R^4$ is ethylene and $n$ is 0 to 10; and alkali metal olefin sulfonates of from 8 to 24 carbon atoms; mixtures thereof; and from 40 to 80% mineral oil; neither the water-soluble foaming organic detergent nor mineral oil being soluble in the other to an extent greater than about 0.1% and the composition having a free moisture content of up to 2%.

These preferred compositions are illustrated, for example, by homogeneous and mutually-insoluble admixtures (50/50 by weight) of sodium coconut-alkyl glyceral ether sulfonate and mineral oil; dimethylhexadecyl amine oxide and mineral oil; sodium salt of sulfonated 1-tetradecene and mineral oil.

An essential aspect of the compositions of the present invention is that they be formulated so as to be substantially anhydrous. For purposes of the present invention, substantially anhydrous compositions are those which have substantially no free or uncombined moisture. Such compositions will have an amount of free or uncombined moisture of less than about 2% by weight of the composition and are considered herein as being substantially anhydrous. Preferably the compositions have less than about 1% free moisture. The presence of free or uncombined moisture, as opposed to that which may be present as water of hydration or water of crystallization, will permit emulsification of the emollient by the detergent component and thereby reduce the efficiency of the detergent/emollient system. Free moisture permits emulsification within the composition itself thereby reducing the amount of oil available for delivery in bath use in the form of a floating layer of oil which can be deposited upon the skin of the bather. It has been found that careful control of both mutual solubility and free moisture content permits delivery of emollient in bathtub use to provide a layer of emollient upon the surface of the bath water. While applicant does not wish to be bound by any theory as to the mechanism by which desirable foaming and formation of a layer of emollient on the water surface is obtained, it is believed that the rapid dissolution of the foaming detergent component to provide a dilute solution of detergent active prevents dispersion or emulsification of the emollient component and thereby permits the emollient to form a film layer on the surface of the bath water and beneath a layer of suds.

The compositions of the invention can be maintained in a substantially anhydrous state by assuring that the detergent and emollient components are themselves substantially anhydrous. The compositions can, however, be maintained in an anhydrous condition by the incorporation of dessicant materials to serve as a moisture sink and thereby prevent moisture pick-up that might tend to promote emulsification within the composition. Thus, the compositions of the invention can contain components having hydratability characteristics so as to provide a moisture sink for free moisture that may come into contact with the compositions of the invention during processing, packaging, storing or the like. Suitable materials include sodium sulfate, magnesium sulfate, the water-soluble carbonates and phosphates such as sodium tripolyphosphate, sodium metaphosphate, sodium sesquicarbonate and the like described hereinbefore. Other examples are described at column 2, line 65 to column 4, line 40 in U.S. Pat. No. 3,451,935 issued June 24, 1969 to Roald et al and incorporated herein by reference.

The compositions of the invention can optionally contain adjuvants, diluents or additives which provide desirable aesthetic qualities or render the compositions more effective. Perfume, for example, can be employed and can be suitably incorporated into the detergent or emollient or added to compositions of the invention in the form of an admixture of perfume oils and inert absorbent powder such as bentonite, starch or powdered milk to minimize contact of the perfume with alkaline components of the compositions. Filler or diluent materials such as urea, sugars, soaps, sodium chloride, sodium sulfate, talc or the like can also be employed. Antimicrobial agents, bacteriostatic agents, dyes, sunscreens, suds builders such as long-chain alkyl amine oxides and fatty acid alkanolamides, suds suppressors and the like can be employed herein without detracting from the advantageous properties of the compositions of the invention.

While the foaming and conditioning compositions of the invention have been described for the most part in connection with their suitability as foaming and skin-conditioning compositions intended for bathing use, the compositions can also be employed as shampoos. Thus, they can be employed for the cleaning of hair so as to effect simultaneously hair conditioning or emollient effects and thereby improve manageability of the hair for grooming. The shampoo compositions will be employed in use by direct application to the scalp but upon addition to water will provide a layer of oil beneath a layer of suds. Accordingly, such compositions are intended as being within the scope of the appended claims.

The following are examples illustrative but not limitative of the compositions of the present invention.

EXAMPLE

A composition containing alkyl glyceryl ether sulphonate paste (96 parts), anhydrous sodium sulphate (3.92 parts) and dye (0.08 parts) was dried by drum drying to a solid flake containing 0.8% of moisture. The flake, in the drum dried form of 2–3 cm. rolls, was further treated by freeze grinding with liquid nitrogen to yield a fine free flowing powder of 0.9% moisture content. The freeze grinding technique involved precooling the surfactant flake with liquid nitrogen prior to mechanical milling by a conventional hammer mill. By this technique the consumption of liquid nitrogen was 1 part per 1 part of flake processed and a grinding temperature of −150° C was reached. The embrittling effect thereby achieved allowed production of a finely divided powder having no material greater than 100 lb. size and a proportion of 80 wt. % finer than 200 lb. The bulk density of this powder was 0.45 gm/cc.

A blend of mineral oil (20 parts), isopropyl myristate (44 parts) and the freeze ground surfactant powder (33 parts) was made with the powder evenly dispersed through the oil phase. The blend was passed once through a colloid mill to give a visually homogeneous product to which perfume (3 parts) was added.

Final product viscosity was 130 cp.

The product made by freeze grinding was tested for dispersability against product made to the same formulation but in which the detergent powder was spray dried. In the freeze ground product the detergent particles had a bulk density of 0.45 gm/cc and were of such size that 92% by weight passed a 100 mesh screen and 80% passed through a 200 lb. screen. The spray dried particles had a bulk density of 0.3 gm/cc and were of such size that 82% of the particles passed through a 100 lb. screen and 30% passed a 200 lb. screen.

A 2 cm. diameter glass tube was filled to 150 cm. depth with water at 110° F. 2 cc. of the spray dried product was introduced into the base of the column of water. Some dispersion of the oil and surfactant components was observed to take place but some particulate aggregates of surfactant rose the full length of the tube and settled on the free surface.

When 2 cc. of the freeze ground product was introduced into a fresh column of water at the same temperature there were no discernable particulate aggregates rising above 30 cm. from the base of the column.

The above shows the superiority of freeze dried particles having a particle size predominately smaller than that corresponding to a 200 mesh screen as opposed to a representative spray-dried product having a larger particle size and a lighter density.

What we claim is:

1. A foaming and conditioning composition providing suds and a layer of emollient oil upon addition to water consisting essentially of a mutually, insoluble mixture of a water-soluble foaming organic detergent and a water-insoluble oily material having skin-softening or emollient properties, neither the detergent nor the oily material being soluble in the other in an amount greater than about 0.1% by weight of the solvent material, the composition being substantially anhydrous, the viscosity of the composition being less than 500 centipoises, and the organic detergent being present at a level of from about 10 to about 60% by weight of the composition, being in the form of finely divided particles containing at least 50% by weight of an organic surfactant selected from the group consisting of anionic, nonionic, cationic, zwitterionic and amphoteric surfactants, and having a moisture content of less than 5% by weight, at least 90% of said particles being of a size to pass a 100 mesh screen and at least 50% of said particles being of a size to pass a 200 mesh screen, and said particles having a bulk density of at least 0.4.

2. The composition of claim 1 wherein the detergent particles contain at least 75% by weight of organic surfactant.

3. The composition of claim 1 wherein the detergent particles contain at least 90% by weight of organic surfactant.

4. A composition according to claim 2 wherein at least 70% of the particles pass through a 200 mesh screen.

5. A composition according to claim 4 wherein the moisture content of the detergent particles is less that 2%.

6. A composition according to claim 5 wherein the moisture content of the detergent particles is less than 1%.

7. A composition according to claim 2 wherein the detergent particles are prepared by freeze-grinding.

8. A composition according to claim 2 wherein the organic surfactant is selected from the group consisting of anionic, nonionic, amphoteric and zwitterionic surfactants.

9. A composition according to claim 8 wherein the water-soluble foaming organic detergent constitutes from 20 to 50% by weight of the composition.

10. A composition according to claim 8 wherein the organic surfactant is selected from the group consisting of alkali metal alkyl glyceryl ether sulfonates wherein the alkyl has from 10 to 18 carbon atoms; amine oxides having a long-chain alkyl radical of from 8 to 24 carbon atoms; alkali metal olefin sulfonates of from 8 to 24 carbon atoms; and mixtures thereof.

11. A composition according to claim 10 wherein the water-soluble foaming organic detergent includes a surface-active material selected from the group consisting of fatty acid monoalkanolamides, fatty acid dialkanolamides and mixtures of fatty acid monoalkanolamides and fatty acid dialkanolamides.

12. A composition according to claim 11 wherein the water-soluble foaming organic detergent includes a mixture of lauric monoethanolamide and lauric diethanolamide in a weight ratio lying between 10 to 1 and 1 to 1.

13. A composition according to claim 2 wherein the oily material having skin-softening or emollient properties is a mineral oil.

14. A composition according to claim 13 wherein the organic surfactant is an alkali metal alkyl glyceryl ether sulfonate wherein the alkyl group has from 10 to 18 carbon atoms.

* * * * *